(12) United States Patent
Gnad et al.

(10) Patent No.: US 8,399,678 B2
(45) Date of Patent: Mar. 19, 2013

(54) PROCESS FOR THE MANUFACTURE OF DABIGATRAN ETEXILATE

(75) Inventors: Frieder Gnad, Bad Kreuznach (DE); Stefan Schmitt, Badenheim (DE); Hermann Mueller-Boetticher, Ober-Hilbersheim (DE); Helmut Heitger, Ingelheim (DE); Siegfried Meineck, Ober-Hilbersheim (DE); Rolf Dach, Gau-Algesheim (DE); Ingo Heddesheimer, Monzingen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 212 days.

(21) Appl. No.: 12/939,521

(22) Filed: Nov. 4, 2010

(65) Prior Publication Data

US 2011/0275824 A1    Nov. 10, 2011

(30) Foreign Application Priority Data

Nov. 18, 2009 (EP) ..................... 09176369

(51) Int. Cl.
*C07D 401/12* (2006.01)
(52) U.S. Cl. .................................. 546/273.4
(58) Field of Classification Search ............... 546/273.4
See application file for complete search history.

(56) References Cited

U.S. PATENT DOCUMENTS

| | | |
|---|---|---|
| 6,358,960 B1 | 3/2002 | Senokuchi et al. |
| 7,202,368 B2 | 4/2007 | Zerban et al. |
| 7,459,566 B2 | 12/2008 | Zerban et al. |
| 7,880,016 B2 | 2/2011 | Zerban et al. |
| 8,119,810 B2 | 2/2012 | Broeder et al. |
| 2006/0004064 A1 | 1/2006 | Zerban et al. |
| 2007/0149589 A1 | 6/2007 | Zerban et al. |
| 2007/0185173 A1 | 8/2007 | Zerban et al. |
| 2007/0185333 A1 | 8/2007 | Zerban et al. |
| 2010/0099882 A1 | 4/2010 | Broeder et al. |
| 2010/0210845 A1 | 8/2010 | Zerban et al. |
| 2011/0118471 A1 | 5/2011 | Filser et al. |
| 2011/0123635 A1 | 5/2011 | Radtke |
| 2011/0129538 A1 | 6/2011 | Landerer et al. |
| 2011/0275824 A1 | 11/2011 | Gnad et al. |
| 2011/0295018 A1 | 12/2011 | Heddesheimer et al. |
| 2012/0116089 A1 | 5/2012 | Broeder et al. |
| 2012/0276206 A1 | 11/2012 | Maier |

FOREIGN PATENT DOCUMENTS

| | | | |
|---|---|---|---|
| WO | 98/37075 | * | 8/1998 |
| WO | 2006000353 A1 | | 1/2006 |
| WO | 2007071742 A1 | | 6/2007 |
| WO | 2007071743 A1 | | 6/2007 |
| WO | 2008095928 A1 | | 8/2008 |
| WO | 2009118321 A1 | | 10/2009 |
| WO | 2009118322 A1 | | 10/2009 |
| WO | 2009153214 A1 | | 12/2009 |
| WO | 2009153215 A1 | | 12/2009 |
| WO | 2010007016 A1 | | 1/2010 |
| WO | 2011061080 A1 | | 5/2011 |

OTHER PUBLICATIONS

International Search Report for PCT/EP2010/066 mailed Feb. 28, 2011.

* cited by examiner

*Primary Examiner* — Patricia L Morris
(74) *Attorney, Agent, or Firm* — Michael P. Morris; Wendy A. Petka

(57) ABSTRACT

An improved process for preparing dabigatran etexilate, as well as analogous compounds of formula 7,

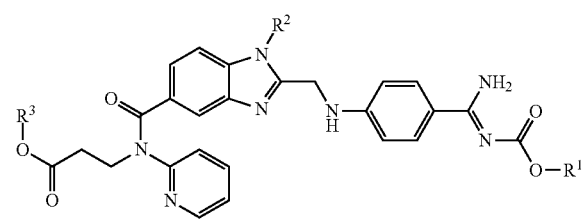

is described.

10 Claims, No Drawings

PROCESS FOR THE MANUFACTURE OF DABIGATRAN ETEXILATE

BACKGROUND TO THE INVENTION

Substituted (4-benzimidazol-2-ylmethylamino)-benzamidines, particularly dabigatran etexilate (CAS 593282-20-3), are already known from International Patent Application WO 98/37075 as active substances with a thrombin-inhibiting and thrombin time-prolonging activity. The main indication sectors of the compound of chemical formula I are the postoperative prophylaxis of deep vein thromboses and stroke prevention (prevention of stroke due to atrial fibrillation, SPAF for short).

In WO 98/37075 it is proposed to produce the substituted (4-benzimidazol-2-ylmethyl-amino)-benzamidines by reacting corresponding substituted (4-benzimidazol-2-ylmethylamino)-benzonitriles with ammonia. This process is extremely onerous from the manufacturing point of view and results in a large quantity of acids that have to be disposed of (cf. also WO 2007/071743, WO 2007/071742).

An improved process for preparing dabigatran etexilate and analogous compounds thereof is described hereinafter. By switching to new starting materials, the use of phase transfer catalysis and the formation of the benzimidazole without the use of coupling reagents a significantly more efficient synthesis of dabigatran etexilate is achieved. The high selectivity in the coupling of the intermediates (step 2) contributes significantly to the economy of the new synthesis route.

DETAILED DESCRIPTION OF THE INVENTION

The present invention describes a process for preparing compounds of formula 7:

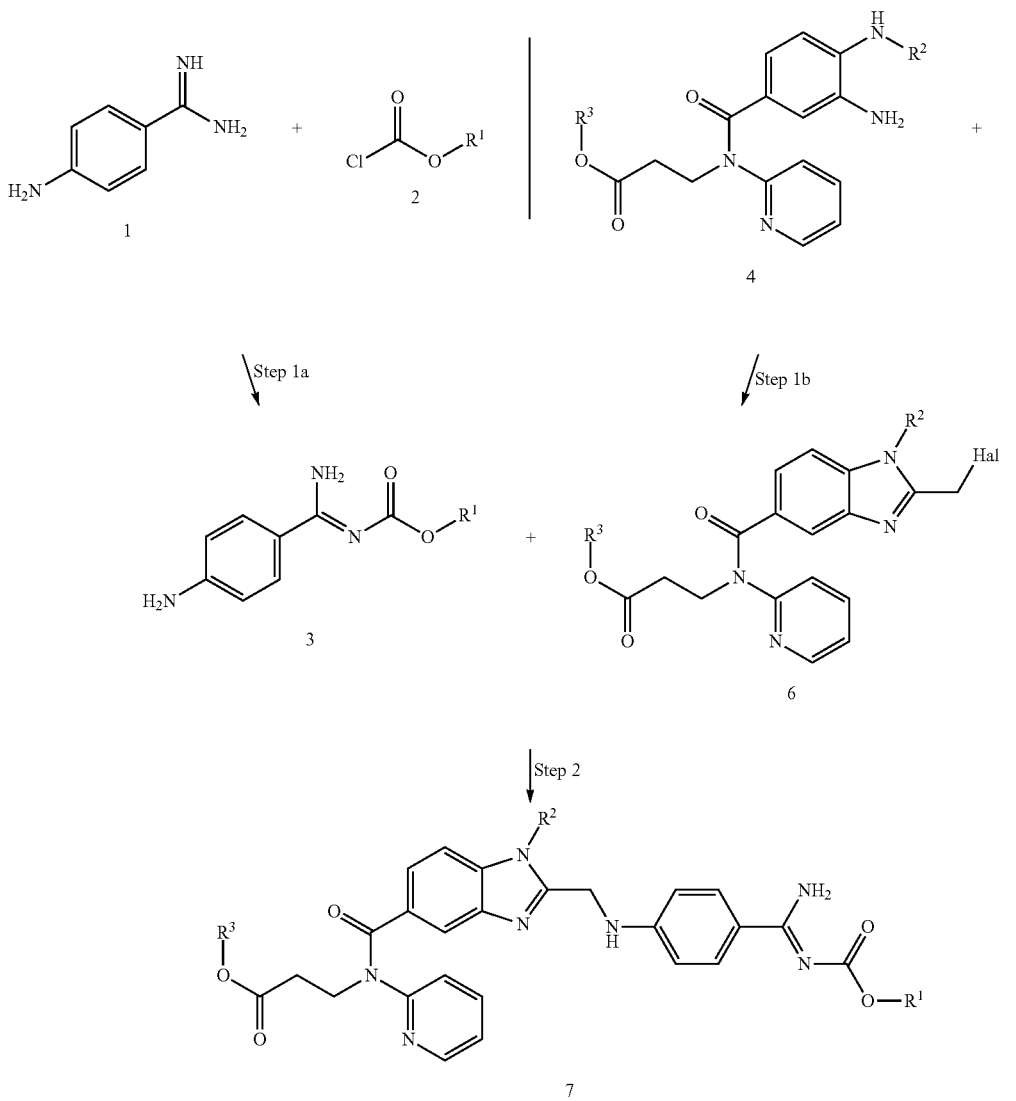

wherein $R^1$, $R^2$ and $R^3$ here and hereinafter each independently of one another denote $C_{1-6}$-alkyl and Hal=chlorine or bromine, preferably chlorine, according to the invention haloacetic acid anhydride 5b-1, haloacetic acid 5b-2, ortho-haloacetate 5b-3 or haloacetyl chloride 5b-4 may be used for 5, and preferably haloacetic acid anhydride 5b-1 or ortho-haloacetate 5b-3 are used for 5.

Preferably $R^1$, $R^2$ and $R^3$ here and hereinafter each represent independently of one another methyl, ethyl, propyl, butyl or hexyl, particularly preferably methyl, ethyl or hexyl, and in particular $R^1$=hexyl; $R^2$=methyl and $R^3$=ethyl.

In Step 1a p-aminobenzamidine 1 and $C_{1-6}$-alkylchloroformate 2 are reacted to form the intermediate 3 (4-aminobenzamidine-$C_{1-6}$-alkyl-carbamate).

Step 1a

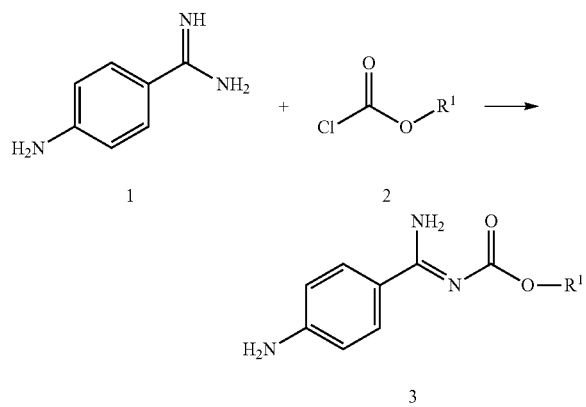

To do this, aminobenzamidine 1, preferably as the hydrochloride, particularly preferably as the dihydrochloride, is cooled in a polar solvent selected from among acetone, ethyl acetate and butyl acetate, preferably acetone, to less than 40° C., preferably 10 to 35° C., particularly preferably 15 to 25° C., particularly 18 to 22° C. Then NaOH or a comparable base and a chloroformate 2 ($R^1$=$C_{1-6}$-alkyl) are added. After the reaction time of about 5 to 30 min, preferably 10 to 20 min, the phases are separated.

The mixture is evaporated down and diluted with a polar solvent selected from among butyl acetate and ethyl acetate, preferably butyl acetate, and purified by extraction with water.

Then the product is precipitated with an acid S selected from among hydrochloric acid, oxalic acid and methanesulphonic acid, preferably hydrochloric acid, and optionally washed with organic solvents selected from among acetone, butyl acetate and ethyl acetate or mixtures thereof, preferably a mixture of acetone and butyl acetate. The preferred mixing ratio of acetone to butyl acetate is 1:1. Compound 3 is obtained as the corresponding salt of the above-mentioned acid S.

In a parallel step 1b compound 4 is reacted with compound 5 to obtain intermediate 6.

Step 1b

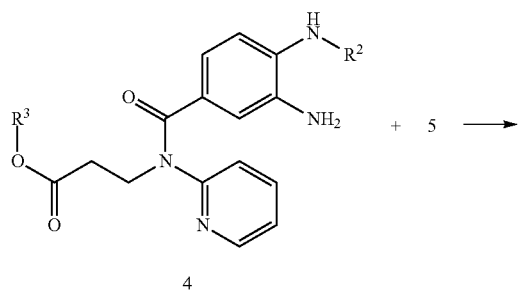

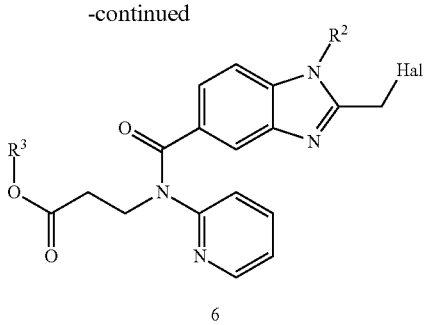

The synthesis of benzimidazoles with carboxylic acid or acid chlorides activated by coupling reagents is known, but has not hitherto been described with a-monochloroacetic acid anhydrides. According to the invention the following compounds may be used for 5:

Variant 1b-1: haloacetic acid anhydride 5b-1;
Variant 1b-2: haloacetic acid 5b-2;
Variant 1b-3: ortho-haloacetate 5b-3, preferably of formula Hal-$CH_3$—$C(OR^4)_3$, ($R^4$ independently of one another denote $C_{1-6}$-alkyl, preferably independently of one another denote methyl or ethyl); 2,2,2-triethoxychloroethane may be mentioned by way of example;
Variant 1b-4: haloacetyl chloride 5b-4.

Where halogen (Hal)=bromine or chlorine, it preferably denotes chlorine. There is no need to isolate the diamine 4 ($R^{2/3}$=$C_{1-6}$-alkyl) beforehand in any of the variants 1b-1, 1b-2, 1b-3 and 1b-4. The product solution may also be reacted from a reaction of reduction of the nitro compound as described in the prior art (cf. WO 98/37075, WO 2007/071743, WO 2007/071742).

For variant 1b-1 the compound 4 is suspended in cooled solvent, the solvent being selected from among ethyl acetate, butyl acetate and tetrahydrofuran, preferably ethyl acetate, and the temperature being below 50° C., preferably 0 to 30° C., particularly preferably 5 to 25° C., particularly 18 to 22° C. Chloroacetic acid anhydride 5b-1' is added to the suspension, for example, and then it is heated to 50 to 80° C., preferably to 55 to 75° C., particularly preferably to 60 to 70° C., particularly to 65° C. After a period of 1 to 6 hours, preferably 1 to 4 hours, particularly preferably 1 to 3 hours, particularly 2 hours, a weak base selected from among potassium carbonate, sodium carbonate and sodium hydrogen carbonate, preferably potassium carbonate, is added at a temperature of 20 to 60° C., preferably 30 to 50° C., particularly preferably 35 to 45° C., particularly 40° C., and the mixture is stirred for a further 30 to 60 min, preferably 40 to 50 min, particularly preferably 45 min. After filtration the filtrate is washed with a solvent selected from among ethyl acetate, butyl acetate and tetrahydrofuran, preferably ethyl acetate, then evaporated down, and precipitated at a temperature of 25 to 65° C., preferably 35 to 55° C., particularly preferably 40 to 50° C., particularly 45° C., by the addition of another solvent selected from among MTBE and tetrahydrofuran, preferably MTBE. The precipitation can be improved by cooling the mixture. The product thus obtained is washed with organic solvents selected from among ethyl acetate, butyl acetate, MTBE and tetrahydrofuran or mixtures thereof, preferably a mixture of ethyl acetate and MTBE. After drying of the filter cake, product 6 is obtained.

Variant 1b-2: molecular sieve (4 Angström) and e.g. chloroacetic acid are added to compound 4 in toluene. The mixture is heated to max. 60° C., preferably 30 to 55° C., particularly preferably to 35 to 55° C., particularly 50° C. and stirred. After a period of 1 to 8 hours, preferably 1 to 6 hours, particularly preferably 1 to 4 hours, particularly 3 hours, the mixture is cooled to max. 20° C. and the product is precipitated. The product thus obtained is washed with toluene. After the filter cake is dried, product 6 is obtained.

For Variant 1b-3 the compound 4 is suspended in a polar solvent selected from among ethyl acetate, butyl acetate and tetrahydrofuran, preferably ethyl acetate, e.g. ortho-chloroacetate 5b-3' and optionally p-toluenesulphonic acid are added and then the mixture is heated to 40 to 80° C., preferably 50 to 70° C., particularly preferably 55 to 65° C., particularly to 60° C. After a period of 1 to 6 hours, preferably 2 to 5 hours, particularly preferably 2.5 to 3.5 hours, particularly 3 hours, the reaction mixture is evaporated down in vacuo, the residue is precipitated with a solvent selected from among MTBE and tetrahydrofuran, preferably MTBE. The precipitation can be improved by cooling the mixture. The product thus obtained is washed with organic solvents selected from among ethyl acetate, MTBE and tetrahydrofuran or mixtures thereof, preferably a mixture of ethyl acetate and MTBE. After the filter cake is dried product 6 is obtained.

For Variant 1b-4 the compound 4 is suspended in a solvent selected from among ethyl acetate, THF and dioxane, e.g. chloroacetyl chloride 5b-4' within 3 h at 50° C. and then made alkaline with NaOH or a comparable base. Then the aqueous phase is separated off and the organic phase is evaporated down, taken up with a polar solvent selected from among butyl acetate and ethyl acetate, the phases are separated and the organic phase is evaporated down again. The residue is precipitated with a solvent selected from among MTBE and tetrahydrofuran. The precipitation can be improved by cooling the mixture. The product thus obtained is washed with organic solvents selected from among butyl acetate, ethyl acetate, MTBE and tetrahydrofuran or mixtures thereof. After the filter cake is dried product 6 is obtained.

The Intermediates 3 and 6 are reacted in Step 2 with phase transfer catalysis and activated with iodide to form compound 7.

Step 2

3 + 6 ⟶

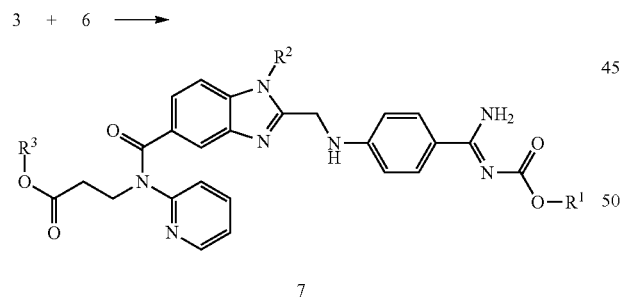

7

The coupling of alkyl chlorides and amidines with iodide ions as catalyst is known, but hitherto this coupling reaction has not been reported to have high selectivity, which is why the syntheses known in the art have switched to doubly protected amidines. Surprisingly a coupling reaction with singly protected p-aminobenzamidine (3) can be carried out with high regioselectivity (>99.7%) using the process described below.

For this purpose, compound 3, together with a base selected from among NaOH, potassium carbonate and sodium carbonate, preferably NaOH, are placed in a mixture of an organic solvent selected from among toluene, tetrahydrofuran, 2-methyltetrahydrofuran, butyl acetate and ethyl acetate, preferably butyl acetate and water and heated to 30 to 65° C., preferably 40 to 60° C., particularly preferably 45 to 55° C., particularly 50° C. Then the phases are separated and optionally the organic phase is extracted once more with water.

The organic phase is combined with compound 6, as well as sodium iodide, sodium hydrogen carbonate, tetrabutylammonium iodide, in cyclohexane and water and then heated to 30 to 60° C., preferably 35 to 50° C., particularly preferably 35 to 45° C., particularly 40° C. After a period of 1 to 6 hours, preferably 1 to 4 hours, particularly preferably 1 to 3 hours, particularly 2 hours, the cyclohexane is distilled off and butyl acetate is added and the mixture is again heated to 50 to 90° C., preferably to 60 to 80° C., particularly preferably to 65 to 75° C., particularly to 70° C. over a period of 1 to 6 hours, preferably 1 to 4 hours, particularly preferably 1 to 3 hours, particularly 2 hours. Then the phases are separated and optionally the organic phase is extracted with water. The organic phase is evaporated down, cooled and filtered. The product thus obtained is washed with organic solvents selected from among butyl acetate and MTBE, preferably butyl acetate or mixtures thereof. After the filter cake is dried product 7 is obtained ($R^{1/2/3}$=$C_{1-6}$-alkyl).

The selectivity and reaction speed are considerably influenced by the above-mentioned solvent system. Particularly when using a two-phase system of water and two different polar organic solvents such as butyl acetate/cyclohexane the reaction can be completed in an outstanding reaction time and with correspondingly high product purity.

Optionally the compound of formula 7 may be converted in a third step into the mesylate 8 analogously to the prior art by reacting 7 with methanesulphonic acid 9.

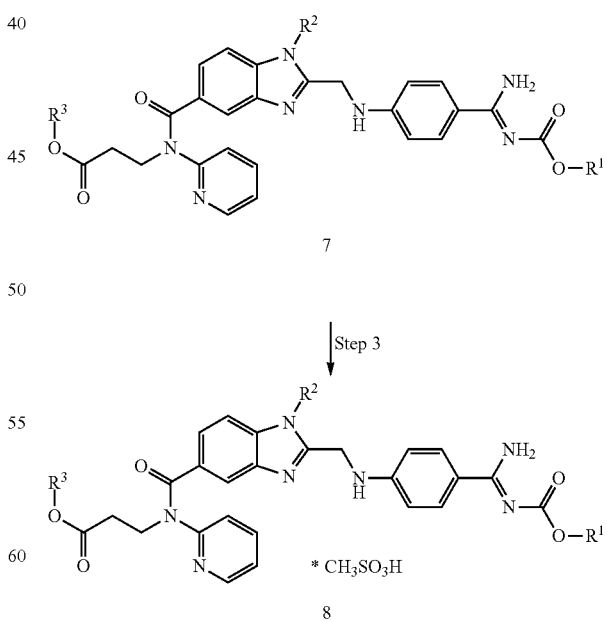

In another aspect the invention relates to the new intermediate products of the above process. This includes compounds of formula 3

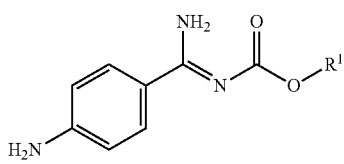

wherein the group $R^1$ denotes $C_{1-6}$-alkyl, preferably methyl, ethyl, propyl, butyl or hexyl, particularly preferably methyl, ethyl or hexyl, particularly n-hexyl.

The invention further relates to compounds of formula 6,

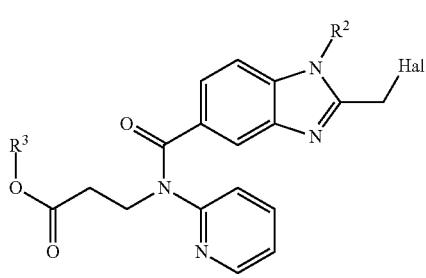

wherein the groups $R^2$ and $R^3$ each independently of one another denote $C_{1-6}$-alkyl, preferably independently of one another denote methyl, ethyl, propyl, butyl or hexyl, particularly preferably methyl, ethyl or hexyl and particularly $R^2$=methyl and $R^3$=ethyl, and also Hal denotes chlorine or bromine, preferably chlorine.

Definitions

By the term "$C_{1-6}$-alkyl" (including those that are part of other groups) are meant branched and unbranched alkyl groups with 1 to 6 carbon atoms and by the term "$C_{1-4}$-alkyl" are meant branched and unbranched alkyl groups with 1 to 4 carbon atoms. Alkyl groups with 1 to 4 carbon atoms are preferred. Examples include: methyl, ethyl, n-propyl, iso-propyl, n-butyl, iso-butyl, sec-butyl, tert-butyl, n-pentyl, iso-pentyl, neo-pentyl or n-hexyl. The abbreviations Me, Et, n-Pr, i-Pr, n-Bu, i-Bu, t-Bu, etc. may optionally also be used for the above-mentioned groups. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By an "organic solvent" is meant, within the scope of the invention, an organic, low-molecular substance which may bring other organic substances into solution by a physical method. The prerequisite for suitability as a solvent is that during the dissolving process neither the dissolving substance nor the dissolved substance must change chemically, i.e. the components of the solution can be recovered in their original form by physical separation processes such as distillation, crystallisation, sublimation, evaporation and adsorption. For different reasons, not only the pure solvents but also mixtures that combine the dissolving properties may be used. Examples include:

alcohols, preferably methanol, ethanol, propanol, butanol, octanol, cyclohexanol;

glycols, preferably ethyleneglycol, diethyleneglycol;

ethers/glycolethers, preferably diethyl ether, tert-butylmethylether, dibutylether, anisol, dioxane, tetrahydrofuran, mono-, di-, tri-, polyethyleneglycolethers;

ketones, preferably acetone, butanone, cyclohexanone;

esters, preferably acetic acid esters, glycolesters;

amides, inter alia nitrogen compounds, preferably dimethylformamide, pyridine, N-methylpyrrolidone, acetonitrile;

sulphur compounds, preferably carbon disulphide, dimethylsulphoxide, sulpholane;

nitro compounds, preferably nitrobenzene;

halohydrocarbons, preferably dichloromethane, chloroform, tetrachloromethane, tri-, tetrachloroethene, 1,2-dichloroethane, chlorofluorocarbons;

aliphatic or alicyclic hydrocarbons, preferably petrol, petroleum ether, cyclohexane, methylcyclohexane, decalin, terpene-L.; or aromatic hydrocarbons, preferably benzene, toluene, o-xylene, m-xylene, p-xylene;

or corresponding mixtures thereof.

EXAMPLES

Step 1A: Synthesis of 4-aminobenzamidine-N-hexylcarbamate

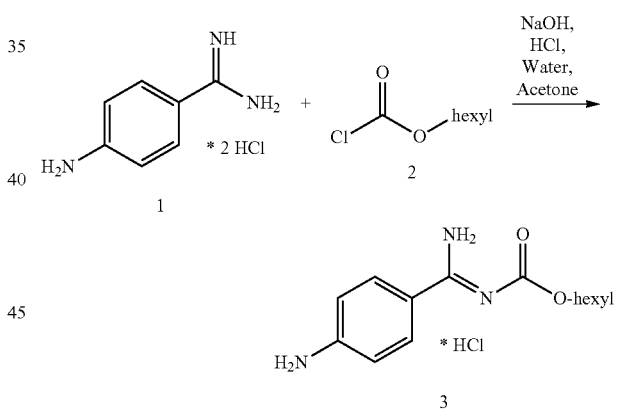

Aminobenzamidine*2HCl (21.2 g) is dissolved in acetone (150 ml), regulated to a temperature of 20° C. and sodium hydroxide solution (80 ml, 4M) is added dropwise. At 20° C. n-hexylchloroformate (16.5 g) is metered in. After rinsing with acetone (20 mL) the mixture is stirred for a further 15 min at 5-10° C. Then the phases are separated. The organic phase is evaporated down in vacuo, diluted with butyl acetate (150 mL) and the phases are separated again. The mixture is once more extracted with water (40 mL) and combined with hydrochloric acid (9, 84 mL, 32%). The residual water is distilled off using the water separator and then evaporated down. The suspension is mixed at 45° C. with acetone (150 mL), cooled to 20° C. and suction filtered. It is washed with a mixture of butyl acetate and acetone (100 mL). The filter cake is dried in vacuo and 29.2 g of product 3 are obtained (97.2% of theoretical).

Step 1B: Synthesis of 6 (8-alanine-N-[[1-methyl-1H-benzimidazole-2-chloromethyl]-5-carbonyl]-N-2-pyridinyl-ethyl ester)

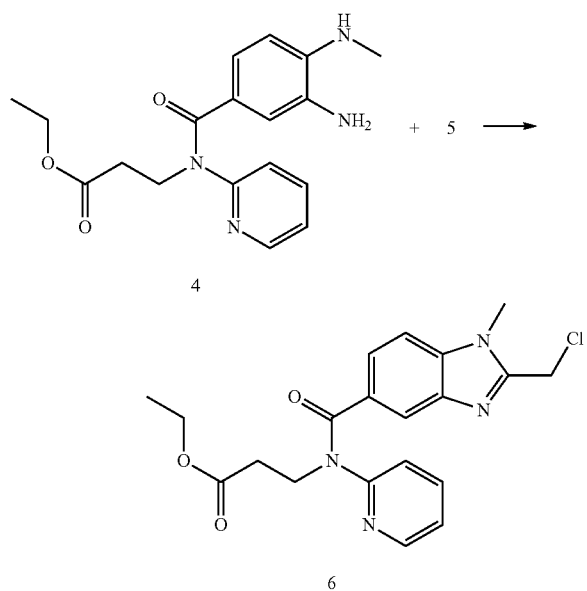

Depending on the synthesis variant, 5 may be chloroacetic acid anhydride 5b-1', chloroacetic acid 5b-2' or a orthochloroacetate 5b-3' or chloroacetyl chloride 5b-4'.

Variant 1b-1: Compound 4 (28.0 g) is suspended in ethyl acetate (120 mL) at 20° C. Then a mixture of ethyl acetate (50 mL) and chloroacetic acid anhydride 5b-1' (14.5 g) is slowly added at 20° C. and then heated to 65° C. After 2 h stirring potassium carbonate (15.0 g) is added at 40° C. and filtered after 45 min. The filter residue is washed with ethyl acetate (8.0 mL). The filtrate is evaporated down in vacuo and precipitated at 45° C. with MTBE (150 mL). It is cooled to −2° C. and filtered. The product is washed with a mixture of ethyl acetate and tert-butylmethylether (MTBE) (50 mL). The filter cake is dried in vacuo and 29.6 g product 6 (90.3% of theoretical) are obtained.

Variant 1b-2: Compound 4 (2 g) in toluene (20 mL) is combined with molecular sieve (4A, 2 g) and chloroacetic acid (2.08 g). The mixture is heated to 50° C. and stirred. After a period of about 3 hours the mixture is cooled to below 20° C. and the product is precipitated. The product thus obtained is washed with toluene. After the filter cake is dried product 6 is obtained (30% of theoretical).

Variant 1b-3: Compound 4 (4.28 g) is suspended in ethyl acetate (26 mL) at ambient temperature and combined with orthochloroacetate 5b-3' (2.79 g) and p-toluenesulphonic acid (0.02 g) and then heated to 60° C. After 3 h stirring the reaction mixture is evaporated down in vacuo, the residue is crystallised with MTBE (25 mL) and filtered. The product is washed with MTBE (25 mL). The filter cake is dried in vacuo and 4.77 g product 6 are obtained (95.2% of theoretical).

Variant 1b-4: Compound 4 (28.0 g) is suspended in THF (80 ml). Then within 2.5 hours a mixture of THF (200 mL) and chloroacetyl chloride 5b-4' (10.0 g) is added at 50° C. and then made alkaline with NaOH (2 mol/l, 50 ml). Then the aqueous phase is separated off and the organic phase is evaporated down and taken up in butyl acetate. The phases are separated again, the organic phase is evaporated down in vacuo and at 45° C. precipitated with MTBE (240 mL). It is cooled to −2° C. and filtered. The product is washed with a mixture of butyl acetate and tert-butylmethylether (MTBE) (50 mL). The filter cake is dried in vacuo and 23.3 g of product 6 are obtained (71% of theoretical).

Step 2: Synthesis of B-alanine-N-[[2[[[4[[[(hexyloxy)carbonyl]4amino]-iminomethyl]phenyl]amino]methyl]-1-methyl-1H-benzimidazol-5yl]carbonyl]-N-2-pyridinyl-ethyl ester

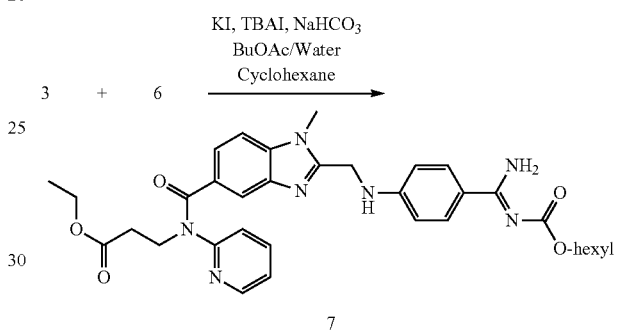

Compound 3 (7.7 g) is placed in butyl acetate (65 mL), sodium hydroxide solution (25 mL, 45%) and water (25 mL) and heated to 50° C. Then the phases are separated and the organic phases are extracted again with water (30 mL). The organic phase is combined with sodium iodide (1.54 g), sodium hydrogen carbonate (4.00 g), tetrabutylammonium iodide (0.75 g), compound 6 (10.0 g), cyclohexane (65 mL) and water (30 mL) and stirred for 2 h at 40° C. Then the cyclohexane is distilled off in vacuo, butyl acetate (95 mL) is added and the mixture is stirred for 2 h at 70° C. Then the phases are separated and the organic phase is extracted twice with water (10 mL). The organic phase is evaporated down in vacuo, the solution is cooled to 0° C. and filtered. The product is washed with butyl acetate (30 mL). The filter cake is dried in vacuo and 13.8 g product 7 are obtained (87.8% of theoretical).

Step 3: β-alanine-N-[[2-[[[4-[[[(hexyloxy)-carbonyl]-4-amino]iminomethyl]phenyl]amino]methyl]-1-methyl-1H-benzimidazol-5yl]carbonyl]-N-2-pyridinyl-ethyl ester-methanesulphonate

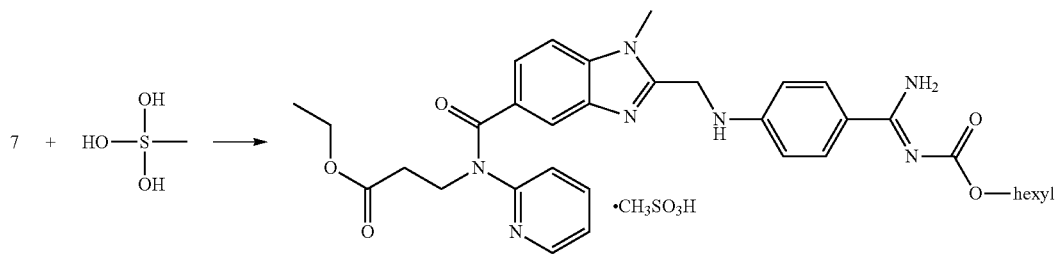

Compound 7 (20 g) is suspended in acetone (238 mL) at ambient temperature and refluxed. The solution is filtered clear and rinsed with acetone (20 mL). The filtrate is cooled to 33° C. and a solution of methanesulphonic acid (3.0 g) in acetone (34 mL) cooled to 0° C. is metered in and the mixture is rinsed with acetone (5.0 mL). Then it is cooled to 20° C. and filtered. The product is washed with acetone (54 mL). The filter cake is dried in vacuo and 22.2 g product 8 are obtained (96.3% of theoretical).

We claim:

1. A process for preparing compounds of formula 7,

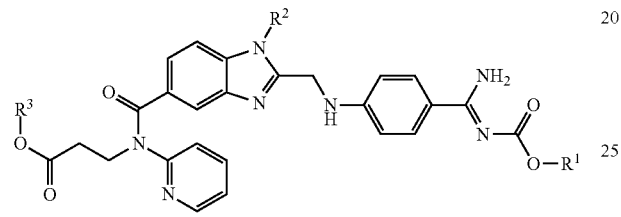

comprising the step of reacting a compound of formula 6

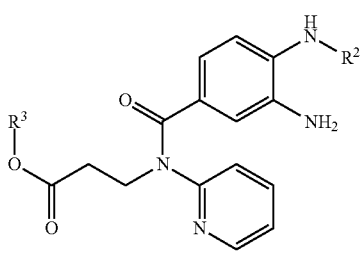

with a compound of formula 3

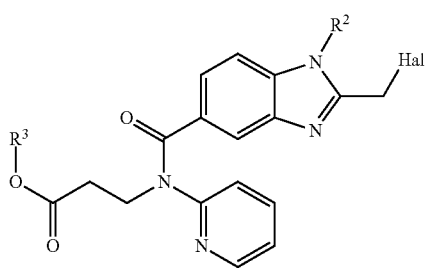

wherein in compounds 7, 6 and 3, $R^1$, $R^2$ and $R^3$ each independently of one another denote $C_{1-6}$-alkyl or halogen (Hal), and wherein Hal is chlorine or bromine.

2. The process according to claim 1, wherein the compound of formula 6

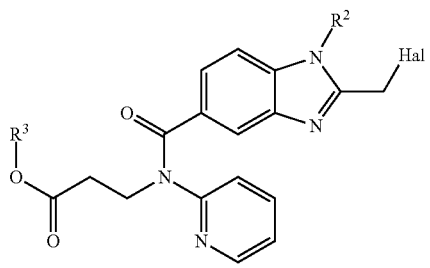

is prepared by reacting a compound of formula 4

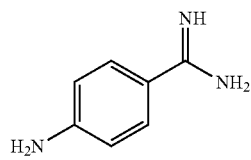

with a compound of formula 5, wherein the compound of formula 5 is selected from among haloacetic acid anhydride 5b-1, haloacetic acid 5b-2, ortho-haloacetate 5b-3 or haloacetyl chloride 5b-4, wherein halogen (Hal) may denote chlorine or bromine, while in the above compounds 4 and 6 the groups $R^1$, $R^2$ and $R^3$ each independently of one another denote $C_{1-6}$-alkyl.

3. The process according to claim 1, wherein the compound of formula 3 is prepared by reacting a compound of formula 1

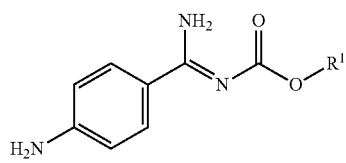

with a compound of formula 2

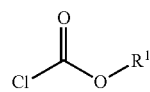

wherein in the above compounds 3 and 2 the groups $R^1$, $R^2$ and $R^3$ each independently of one another denote $C_{1-6}$-alkyl.

4. The process according to claim 1, wherein the groups $R^1$, $R^2$ and $R^3$ each independently of one another represent methyl, ethyl, propyl, butyl or hexyl.

5. The process according to claim 1, wherein the groups $R^1$ is hexyl; $R^2$ is methyl and $R^3$ is ethyl.

6. The process according to claim 2, wherein the compound of formula 5 is selected from among chloroacetic acid anhydride 5b-1', chloroacetic acid 5b-2', orthochloroacetate 5b-3' or chloroacetyl chloride 5b-4'.

7. The process according to claim 2, wherein the compound of formula 5 is selected from among chloroacetic acid anhydride 5b-1' or orthochloroacetate 5b-3'.

8. The process according to claim 1, wherein the reaction of the compound of formula 6 is carried out with a compound of formula 3 in a two-phase solvent system consisting of water and an organic solvent which is immiscible therewith.

9. The process according to claim 8 wherein the reaction of the compound of formula 6 is carried out with a compound of formula 3 in a two-phase solvent system consisting of water and one or more solvents selected from among toluene, tetrahydrofuran, 2-methyltetrahydrofuran, butyl acetate, cyclohexane and ethyl acetate.

10. The process according to claim 1 wherein the compound 7 is reacted with methanesulphonic acid 9 to form a compound of formula 8

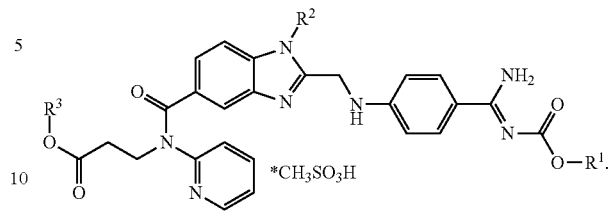

* * * * *